US009019106B2

(12) United States Patent
Alameh et al.

(10) Patent No.: US 9,019,106 B2
(45) Date of Patent: Apr. 28, 2015

(54) ADAPTIVE WEARABLE DEVICE FOR CONTROLLING AN ALARM BASED ON USER SLEEP STATE

(75) Inventors: Rachid Mohsen Alameh, Crystal Lake, IL (US); William Paul Alberth, Jr., Prairie Grove, IL (US); Phillip David Rasky, Buffalo Grove, IL (US)

(73) Assignee: Google Technology Holdings LLC, Mountain View, CA (US)

( * ) Notice: Subject to any disclaimer, the term of this patent is extended or adjusted under 35 U.S.C. 154(b) by 190 days.

(21) Appl. No.: 13/327,113

(22) Filed: Dec. 15, 2011

(65) Prior Publication Data

US 2013/0154838 A1 Jun. 20, 2013

(51) Int. Cl.

| | |
|---|---|
| ***G08B 23/00*** | (2006.01) |
| ***G04G 13/02*** | (2006.01) |
| ***G04G 21/02*** | (2010.01) |
| *G08B 21/00* | (2006.01) |
| *A61B 5/08* | (2006.01) |
| *A61B 5/00* | (2006.01) |

(52) U.S. Cl.

CPC .............. *G04G 13/023* (2013.01); *G04G 21/02* (2013.01)

(58) Field of Classification Search

CPC ......... G08B 21/06; G08B 25/008; A61B 5/18
USPC ...................... 340/575, 870.09; 600/534, 301
See application file for complete search history.

(56) References Cited

U.S. PATENT DOCUMENTS

| | | | | |
|---|---|---|---|---|
| 7,415,100 | B2 | 8/2008 | Cooper et al. | |
| 7,460,899 | B2 | 12/2008 | Almen | |
| 7,898,426 | B2 * | 3/2011 | Rai et al. | 340/575 |
| 8,766,805 | B2 | 7/2014 | Alameh et al. | |
| 2001/0028309 | A1 | 10/2001 | Torch | |
| 2007/0273506 | A1 * | 11/2007 | Butler | 340/539.18 |
| 2008/0027337 | A1 * | 1/2008 | Dugan et al. | 600/508 |
| 2009/0273478 | A1 * | 11/2009 | Mei | 340/575 |
| 2011/0029044 | A1 * | 2/2011 | Hyde et al. | 607/62 |
| 2011/0037594 | A1 | 2/2011 | Ou Yang et al. | |
| 2011/0077548 | A1 * | 3/2011 | Torch | 600/558 |
| 2011/0230790 | A1 * | 9/2011 | Kozlov | 600/595 |
| 2011/0245633 | A1 * | 10/2011 | Goldberg et al. | 600/301 |
| 2012/0253220 | A1 * | 10/2012 | Rai et al. | 600/544 |

OTHER PUBLICATIONS

Walter Karlen, "Adaptive Wake and Sleep Detection for Wearable Systems", 2009, 185 pages.

Wakemate, "The Basics", http://www.wakemate.com/tour/, Accessed Dec. 15, 2011, 1 page.

(Continued)

*Primary Examiner* — Jack K Wang
(74) *Attorney, Agent, or Firm* — Shumaker & Sieffert, P.A.

(57) ABSTRACT

A method is provided for dismissing or altering a user-configured alarm upon detection of the user's sleep state. The method includes associating an alarm device with the user's body by securing a wearable device to the user's wrist, placing the device in a pocket, integrating the device into the user's clothing such as a belt, or otherwise placing the device in contact with or adjacent to the user. The device includes one or more sensors for detecting physiological and/or environmental parameters such as heart, respiration, or pulse rate, body movements, eye movements, ambient light, and the like. If the user is asleep, the alarm is actuated in a typical manner. If the user is awake, the alarm is suppressed. If the user is neither asleep nor fully awake, the alarm is adjusted to provide an appropriate level of stimulation.

22 Claims, 3 Drawing Sheets

(56) References Cited

OTHER PUBLICATIONS

Sleeptracker, "the Key to Waking Up Refreshed", 4 pages, http://www.electronichealing.co.uk/sleeptracker.htm, Accessed Dec. 15, 2011.

Appbrain, "Gentle Alarm," Mobitobi, Jul. 18, 2011, 2 pp., retrieved from http://www.appbrain.com/app/gentle-alarm/com.mobitobi.android.gentlealarm.

Appbrain, "Sleep Now!," Mobitobi, Jul. 18, 2011, 2 pp., retrieved from http://www.appbrain.com/app/sleep-now/com.mobitobi.android.sleepnow.

* cited by examiner

ADAPTIVE WEARABLE DEVICE FOR CONTROLLING AN ALARM BASED ON USER SLEEP STATE

TECHNICAL FIELD

The present disclosure relates generally to wearable devices, and more particularly to wearable devices and methods for dismissing an alarm when it is detected that the user is awake.

BACKGROUND

Modern electronic devices include increased functionality as technologies converge on single platforms. For example, computers, mobile phones, personal digital assistants, music players, video players, televisions, and network technology are being encompassed on a single device. These devices are being built smaller and smaller, and they may incorporate multiple input mechanisms such as one or more keys and a touch-screen as well as proximity and image-based input components. Such devices may include portable computers, cellular telephones and smart phones and perform a number of functions, including receiving emails and other messages, playing audio and video content, and signaling an audible or haptic alarm.

BRIEF SUMMARY

In an exemplary embodiment, a method of dismissing or adjusting an alarm if the user is determined to be awake is provided. The method includes sensing a physiological parameter of the user through a wearable device, detecting whether the user is awake, and adjusting the alarm in accordance with the user's sleep state.

In another exemplary embodiment, a wireless communication device for a user is provided. The device includes a wearable device for adjusting or dismissing an alarm based on the detected sleep state of the user. The device includes a display module for facilitating user interaction, a sensor for detecting a sleep state of the user, an alerting module for alerting the user, and a controller coupled to the display module, the sensor, the memory module, and to the alerting module. The controller is configured to receive sensed data associated with the sleep state of the user, and thereafter actuate or adjust the output of the alerting module based upon the sleep state of the user.

In one exemplary embodiment, a method of dismissing a previously set alarm, if the user is determined to be awake, is provided. The method includes sensing a physiological parameter of the user through an alarm device proximate the user's body, detecting the sleep state of the user, and dismissing or adjusting the alarm based on the user's sleep state.

In another exemplary embodiment, a wireless communication device for a user is provided. The device includes a wearable device for alerting a user of a scheduled event, such as being awakened by an alarm at a predetermined point in time. The device includes a display module for facilitating user interaction, at least one sensor for detecting a sleep state of the user, an alerting module for alerting the user, and a controller coupled to the display module, the sensor, the memory module, and to the alerting module. The controller is configured to actuate, suppress, or adjust an alarm signal to the alerting module upon receipt of a data from the sensor indicative of the user's sleep state.

Furthermore, other desirable features and characteristics will become apparent from the subsequent detailed description and the appended claims, taken in conjunction with the accompanying drawings and this background.

BRIEF DESCRIPTION OF THE DRAWINGS

The present disclosure will hereinafter be described in conjunction with the following drawing figures, wherein like numerals denote like elements, and wherein.

DETAILED DESCRIPTION

The following detailed description is merely exemplary in nature and is not intended to limit the application and uses of the wearable device described herein. Furthermore, there is no intention to be bound by any theory presented in the preceding background or the following detailed description.

Broadly, exemplary embodiments disclosed herein provide a device for detecting the sleep state of a person wearing the device, and to actuate an alarm to awaken the user at a user-selected point in time when the user anticipates being asleep. When the predetermined time for awakening arrives, the device determines whether the user is asleep based on the detection of one or more sensed biological and/or physiological parameters. If the user is asleep at the scheduled awakening time, the alarm is actuated in the normal course. If, however, the device determines that the user is awake, the alarm may be dismissed, postponed, or otherwise altered. In this regard, the alarm module may be on-board the device and/or remote (off-board) from the device, e.g., wirelessly coupled to the device.

Figure 1A:
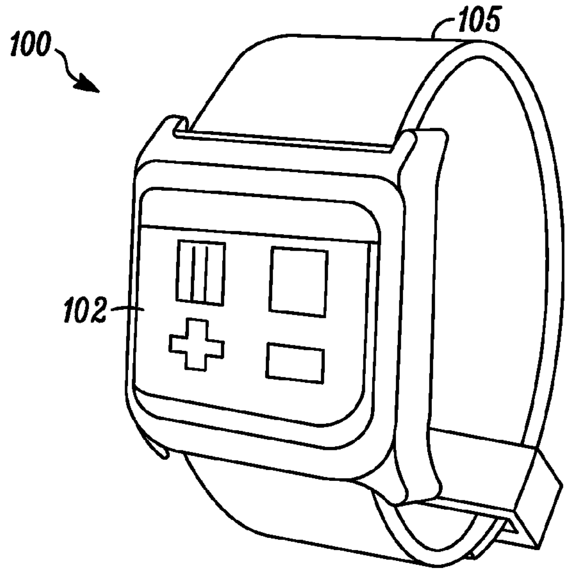
FIG. 1A is a front view of a wearable alarm device in accordance with an exemplary embodiment.

FIG. 1A is a front view of a wearable device 100 in accordance with an exemplary embodiment. Although exemplary embodiments are discussed below with reference to wearable devices, the systems and methods discussed herein are equally applicable to any type of device. In the illustrated exemplary embodiment, the device 100 is in the form of a watch having a watch face which may be configured as a modified "desktop" interface. Device 100 includes a device module 102 and an attachment band 105 for attaching the device to the user's wrist, upper arm, neck, leg (e.g., thigh or ankle), waist, head, or the like. Band 105 may be a single or multi-piece belt or strap, and may be stiff, flexible, elastic, or adjustable to accommodate the particular mode of attachment. In a further embodiment, device module 102 may be worn as a pendant, broach, headband, or may be sewn, stitched, fastened to or otherwise integrated into the user's clothing, cap, undergarments, or the like.

Figure 1B:
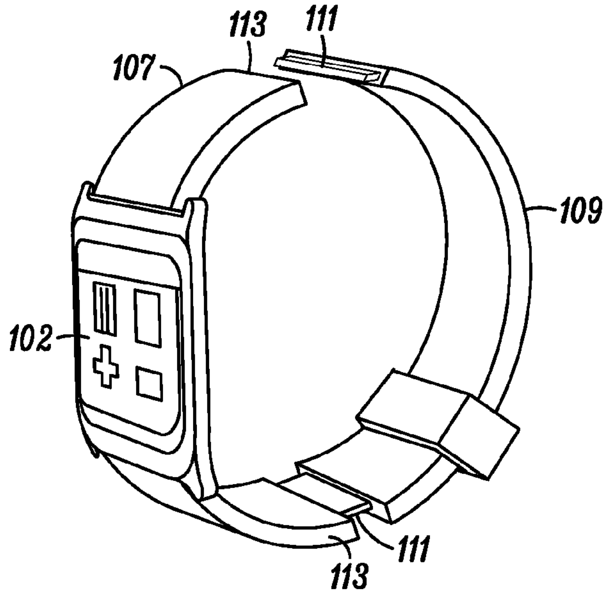
FIG. 1B is a side view of the wireless device of FIG. 1 in accordance with an exemplary embodiment.

FIG. 1B shows a detachable strap having a first part 107 connected to device module 102 and a second part 109 releasably fastened to first part 107. For this purpose, first part 107 includes a clasp portion 113 and second part 109 includes a mating clasp portion 111. Respective clasp portions 111 and 113 may be releasably fastened together to secure device 100 to a user's body. Alternatively, one or both parts 107, 109 may be separated from device module 102 to facilitate placement in a pocket, hood, sleeve, or the like.

Device module 102 may be embodied, for example, in a device such as a cellular phone, smart phone, MP3 player, iPod™ player, personal digital assistant (PDA), mobile handset, personal computer (PC), gaming device, security device, wellness device, alarm clocks, portable device, television, radio, or the like. In the illustrated exemplary embodiment, device 100 is in the form of a wrist watch. Alternatively, the device may be configured in any convenient manner to permit monitoring and/or detection of one or more parameters associated with the sleep state of the user.

The device 100 may be, for example, a handheld wireless device, such as a mobile phone, a Personal Digital Assistant (PDA), a smart phone, tablet or laptop computer, a multimedia player, a MP3 player, a digital broadcast receiver, remote controller, or any other electronic apparatus. Many embodiments may be portable and hand-held, but this is not required. In one exemplary embodiment, the device 100 is a cellular phone that exchanges information with a network (not shown). The network may be, for example, a wireless telecommunication network, the Internet, a public switched-phone network, and the like, and the type of information exchanged with the network may include voice communication, digital data, SMS messaging, MMS messaging, Internet access, multi-media content access, voice over internet protocol (VoIP), and other conventional communication standards and protocols.

More particularly, a number of parameters may be monitored and evaluated in order to ascertain, or infer, the user's sleep state. For example, a video camera or other hardware for capturing image data may be used to detect the user's eyes closing, blinking frequency, or head nodding. A pre-sleep or sleep state may also be detected based on EEG patterns, or inferred from various physiological, environmental and/or contextual circumstances such as the user changing into pajamas, brushing teeth, brushing hair, getting into bed, pulling covers over the user's body, galvanic skin response, thermal sensing (e.g., skin temperature), ambient light, temperature, heart rate profile, breathing profile, or background noise or motion.

Figure 2:
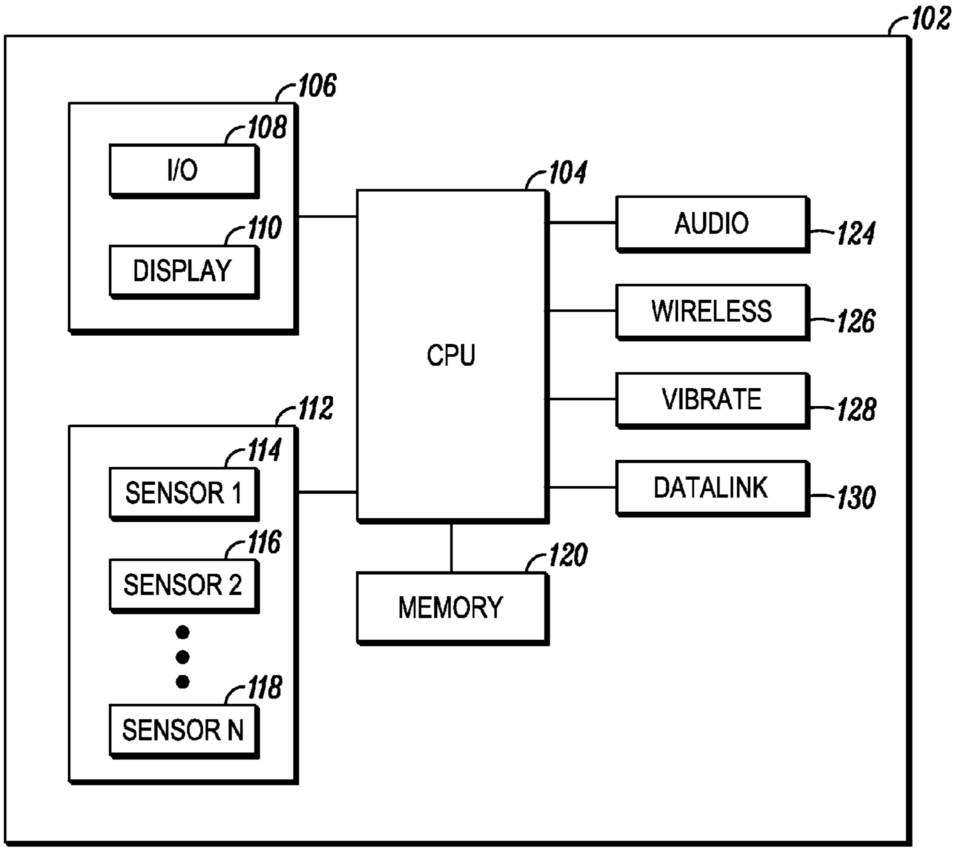
FIG. 2 is a block diagram a wireless device in accordance with an exemplary embodiment.

FIG. 2 is a block diagram of the device 102 of FIGS. 1A & 1B in accordance with an exemplary embodiment. In one implementation, the device includes a controller 104, a memory 120, a user interface 106 including a user input module 108 and a display 110, and a sensor module 112 including respective sensors 114-118. User input (or I/O) module 108 may include one or more of a touch-sensitive, numeric keypad, or traditional "QWERTY" keyboard implemented in hardware or as a screen display.

Sensors 114-118 may include one or more of an accelerometer or motion sensor 114, and ambient environment sensor 116 for sensing one or more of ambient light, GPS position coordinates, motion, sound, temperature, video, pattern recognition, and the like, and a physiological data sensing module 118 for sensing one or more of skin temperature, moisture, electrical conductivity/resistivity, pulse oxymetry, pulse rate, blood pressure, heart rate, respiration, voice recognition, video pattern recognition, and the like.

The embodiment illustrated in FIG. 2 further includes one or more output modules such as, for example, an audio module 124, a communications module 126 such as a cellular transceiver or wireless network interface (e.g., Bluetooth, WiFi), a vibration module 128, a wireless interface to a light blinking device (e.g., and LED), and a data link 130 such as a USB, fire wire, or other suitable data port.

In general, the controller 104 controls the operation of the device 102 in accordance with computer instructions stored in memory 120. The controller 104 may be implemented using a digital signal processor, microprocessor, microcontroller, programmable logic unit, discrete circuits, or a combination thereof.

The memory 120, coupled to the controller 104, stores software programs for performing the functions described herein, including operation of the device 100, an operating system, various application programs, and data files. The memory 120 can include one or more forms of volatile and/or non-volatile, fixed and/or removable memory, such as read-only memory (ROM), electronic programmable read-only memory (EPROM), random access memory (RAM), and erasable electronic programmable read-only memory (EEPROM).

The memory 120 may include random access memory, read only memory, optical memory, or any other type of memory. The memory 120 may be arranged and configured to store information to be used by other components of the device module 102, including the user interface 106, the sensor module 112, the audio module 124, wireless communications module 126, vibration module 128, and data link 130.

In an exemplary embodiment, the memory 120 may be configured to store information pertaining to a user-selected point in time at which the user desires an alarm to be actuated, for example to awaken the user at a point in time in the future when the user expects to be asleep. Memory 120 may thus include a calendar, a schedule, a task or "to do" list, and the like.

The alarm settings may be fetched from on-board memory 120 or downloaded from remote sources, for example, through wireless module 126 and/or data link 130. That is, although the controller 104 and memory 120 are illustrated within the device module 102, the processing and storage capabilities may be distributed and accessed from one or more networks or external storage devices. Depending on the embodiment, additional components may be provided or certain components omitted. The device module 102 may be assembled from discrete components, or implemented in one or more integrated circuits, or it may be assembled from a combination of discrete components and integrated circuit components.

In general, the controller 104 is implemented as a processor, computer, integrated circuit, or the like controlled by software or firmware. The controller 104 communicates with sensor module 112 to obtain and interpret physiological and/or environmental information, as well as from I/O module 108 and memory 120, and evaluates received information to determine whether the user is asleep, awake, or in a pre- or post-sleep state in which the user is neither asleep nor fully awake.

When the system determines that the user is asleep (or otherwise not fully awake) at the scheduled alarm time, the system actuates the alarm module in accordance with the desired user settings, including directing display 110 to alert the user with a visual image such as: "wake up now" or "wake up in ten minutes", or the like. The system may alternatively remind, alert, or query the user using one or a combination of visual signals, haptic signals including vibration module 128, and/or audio signals (such as an alarm or a verbal reminder) to an audio speaker associated with sound module 124.

The device module 102 may also include a variety of other components (not shown) based on the particular implementation. For example, if the device module 102 is implemented as a mobile phone, it would also include a microphone and a wireless transceiver and possibly additional input components such as a keypad, accelerometer, and vibration alert. If the device module 102 is implemented as a remote controller, an infrared transmitter could also be included.

As noted above, the device module 102 may be a communications device that supports various communication functions, including telephony, email, and web-browsing. As such, the controller 104 may control the device module 102 to transmit, receive, modulate, or demodulate communications to and from a network, including wide area networks (WAN), such as cellular networks, local area networks (LAN), personal area networks (PAN), or any other type of network. These functions may be facilitated by the audio module 124 and the wireless communications module 126 and data link 130. The wireless module 126 may include a transceiver, transmitter or receiver such that the device module 102 may communicate with a wireless or cellular network. The audio module 124 may include a microphone, a speaker, a transducer, or any audio input and output circuitry for converting audible signals to and from digital signals.

As introduced above, the device module 102 includes a display 110 and an I/O module 108. The display 110 may include a liquid crystal display (LCD) or other suitable device to display information to the user, while the I/O 108 may include a keyboard, keys, touchscreen input, or combination of input mechanisms for receiving and making telephone calls and supporting other interactions between the user and the device 100. In some embodiments, the display 110 and I/O module 108 may be combined, for example, in a touch screen display configured to receive user input using a finger stylus.

Figure 3:
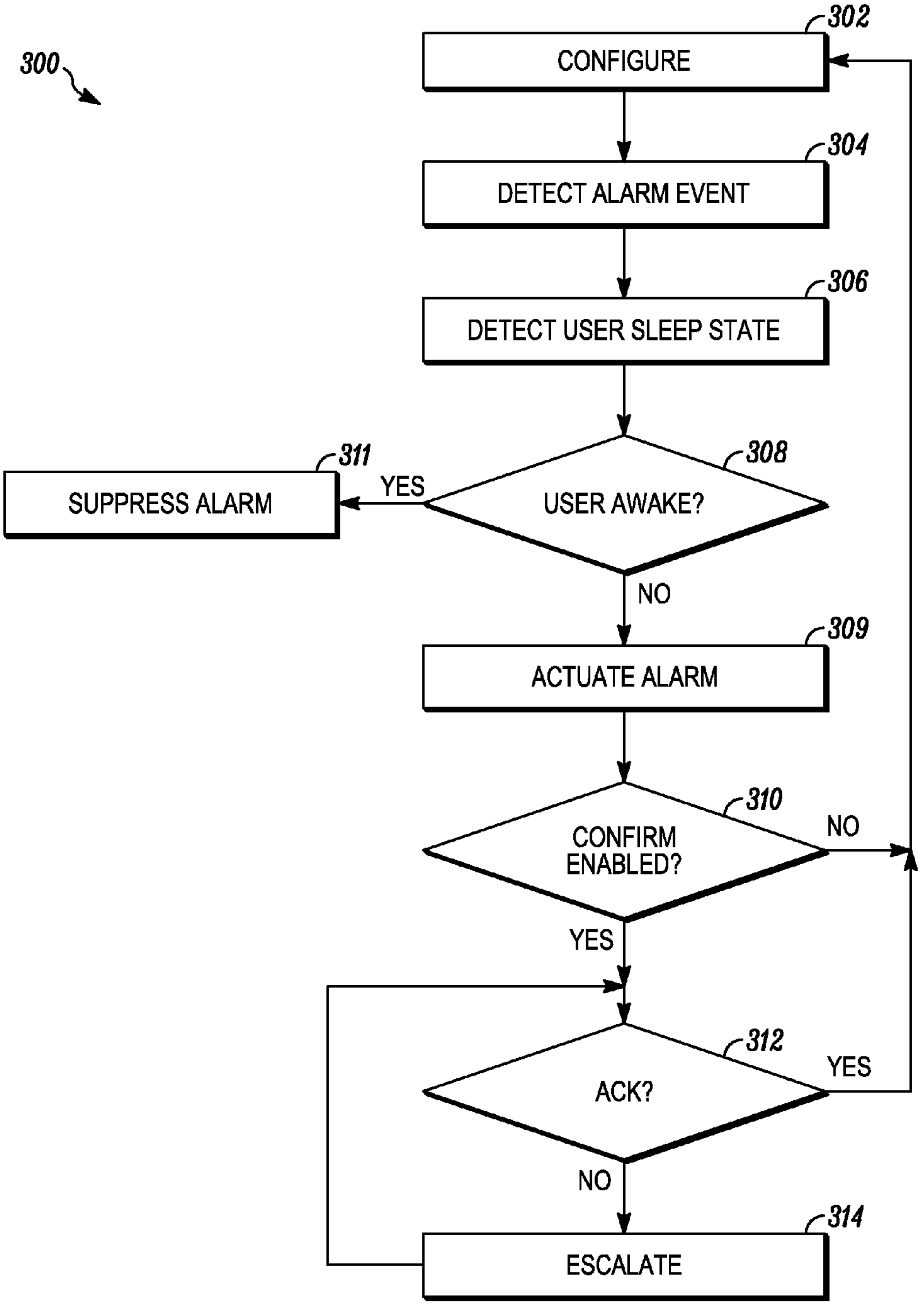
FIG. 3 is a flowchart illustrating the method of operation of the device of FIGS. 1-3 in accordance with an exemplary embodiment.

FIG. 3 is a flowchart of a method 300 for operating the device module 102 in accordance with an exemplary embodiment. The device module 102 is initially configured (task 302) to establish operational parameters such as, for example: enabling sleep state detection: enabling a confirmation function (discussed below); and defining the alarm modality (e.g., screen display, audible alarm, vibration).

Upon detection of a scheduled alarm event (task 304), the system determines (task 306) the sleep state of the user. If the user is awake ("Yes" branch from decision 308), the alarm is suppressed (task 311). If the user is not awake ("No" branch from decision 308) the alarm is actuated (task 309). As discussed above, the alarm may be actuated by presenting the user with one or more of: an audio signal via audio module 124; a haptic stimulus via vibration module 128; displaying a graphic and/or textual message via display 110.

In an embodiment, the system allows the user to selectively enable a confirmation function in connection with configuration task 302. If this function is not enabled, the system simply passively alerts the user of assembled tasks to be attended to prior to going to sleep. If the confirmation option is selected, the system requires the user to confirm or acknowledge the alarm to ensure that the user is awake. Thus, the system delivers one or more increasingly escalating alerts until the alert is acknowledged (confirmed) by the user. The escalating alerts may take the form of audio and/or vibration alerts of increasing amplitude, frequency, and/or duration.

Referring again to FIG. 3, if the confirmation function is not enabled ("No" branch from task 310), following the delivery of an alert or reminder to the user the system returns to an initial state (e.g., to task 302) and waits for the next alarm event. If confirmation is enabled ("Yes" branch from task 310), the system interrogates the user (task 312) for an acknowledgement that the user is awake. Upon receiving such an acknowledgement ("Yes" branch from task 312), the system resumes an initial state (e.g., task 302). If an acknowledgement is not timely received ("No" branch from task 312), the system delivers one or more increasingly escalating alerts (task 314) until the alarm is acknowledged or otherwise attended to ("Yes" branch from task 312).

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration in any way. Rather, the foregoing detailed description will provide those skilled in the art with a convenient road map for implementing various embodiments. It being understood that various changes may be made in the function and arrangement of elements described in an exemplary embodiment without departing from the scope of the invention as set forth in the appended claims.

It is further understood that the use of relational terms such as first and second, top and bottom, and the like, if any, are used solely to distinguish one from another entity, item, or action without necessarily requiring or implying any actual such relationship or order between such entities, items or actions. Much of the inventive functionality and many of the inventive principles are best implemented with or in software programs or instructions. It is expected that one of ordinary skill, notwithstanding possibly significant effort and many design choices motivated by, for example, available time, current technology, and economic considerations, when guided by the concepts and principles disclosed herein will be readily capable of generating such software instructions and programs with minimal experimentation. Therefore, further discussion of such software, if any, will be limited in the interest of brevity and minimization of any risk of obscuring the principles and concepts described herein.

As understood by those in the art, controller 104 includes a processor that executes computer program code to implement the methods described herein. Embodiments include computer program code containing instructions embodied in tangible media, such as floppy diskettes, CD-ROMs, hard drives, or any other computer-readable storage medium, wherein, when the computer program code is loaded into and executed by a processor, the processor becomes an apparatus for implementing the methods and apparatus described herein.

Embodiments of the various techniques described herein may be implemented in digital electronic circuitry, or in computer hardware, firmware, software, or in combinations of them. Embodiments may be implemented as a computer program product, i.e., a computer program tangibly embodied in an information carrier, e.g., in a machine-readable storage device or in a propagated signal, for execution by, or to control the operation of, data processing apparatus, e.g., a programmable processor, a computer, or multiple computers. A computer program, such as the computer program(s) described above, can be written in any form of programming language, including compiled or interpreted languages, and can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Generally, a computer also may include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory may be supplemented by, or incorporated in special purpose logic circuitry.

Method steps may be performed by one or more programmable processors executing a computer program to perform functions by operating on input data and generating output. Method steps also may be performed by, and an apparatus may be implemented as, special purpose logic circuitry, e.g., an FPGA (field programmable gate array) or an ASIC (application-specific integrated circuit).

It will be appreciated that the above description for clarity has described various embodiments with reference to different functional units and processors. However, it will be apparent that any suitable distribution of functionality between different functional units or processors may be used. For example, functionality illustrated to be performed by separate processors or controllers may be performed by the same processor or controllers. Hence, references to specific functional units are only to be seen as references to suitable means for providing the described functionality rather than indicative of a strict logical or physical structure or organization.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the devices and methods described herein. Rather, the foregoing detailed description will provide those skilled in the art with a convenient road map for implementing exemplary embodiments. It being understood that various changes may be made in the function and arrangement of elements described in an exemplary embodiment without departing from the scope of the invention as set forth in the appended claims.

What is claimed is:

1. A method comprising:

determining, at a user-selected point in time and based on at least one physiological parameter detected by a sensor coupled to a wearable device, a sleep state of a user of the wearable device; and responsive to determining, based on the sleep state, that the user is currently asleep:

actuating the alarm; and responsive to determining that the user has not acknowledged the alarm within a predetermined time period, outputting two or more alerts in which each respective successive alert of the two or more alerts has at least one of a greater amplitude, frequency, or duration than each respective prior alert of the two or more alerts, wherein the two or more alerts are output until the user has acknowledged at least one of the two or more alerts.

2. The method of claim 1, wherein the at least one physiological parameter of the user comprises user limb movement data.

3. The method of claim 1, wherein the at least one physiological parameter of the user comprises at least one of galvanic skin response data, pulse oxymetry data, heart rate data, or respiration data.

4. The method of claim 1, wherein the alarm is connected to and on-board the device.

5. The method of claim 1, wherein the alarm is remote from and off-board the device.

6. The method of claim 1, wherein determining the sleep state of the user comprises recognizing, based on the at least one physiological parameter of the user, a pattern associated with eyes of the user.

7. The method of claim 1, wherein determining the sleep state of the user comprises determining, based on the at least one physiological parameter of the user, whether eyelids of the user are closed.

8. The method of claim 1, wherein determining the sleep state of the user comprises determining, based on the at least one physiological parameter of the user, a nodding of a head of the user.

9. The method of claim 1, wherein determining the sleep state of the user comprises determining, based on the at least one physiological parameter of the user, a skin temperature of the user.

10. The method of claim 1, wherein actuating the alarm comprises providing at least one of an audible alarm, a vibration alert, a blinking of a light-emitting diode, or a display of text.

11. The method of claim 1, wherein the two or more alerts comprise a plurality of audio or vibration alerts that are output until the user has acknowledged at least one of the plurality of audio or vibration alerts.

12. A method comprising:

determining, at a user-selected point in time and based on at least one physiological parameter detected by a sensor coupled to a wearable device, a sleep state of a user of the wearable device;

responsive to determining, based on the sleep state, that the user is currently asleep:

actuating the alarm; and responsive to determining that the user has not acknowledged the alarm within a predetermined time period, outputting two or more alerts in which each respective successive alert of the two or more alerts has at least one of a greater amplitude, frequency, or duration than each respective prior alert of the two or more alerts, wherein the two or more alerts are output until the user has acknowledged at least one of the two or more alerts; and responsive to determining, based on the sleep state, that the user is currently awake, suppressing actuation of the alarm.

13. A device comprising:

a controller;

a sensor coupled to the controller, wherein the sensor detects at least one physiological parameter of a user;

wherein the controller is configured to:

determine, at a user-selected point in time and based on the at least one physiological parameter of the user, the sleep state of the user; and responsive to determining, based on the sleep state, that the user is currently asleep:

actuate the alarm; and responsive to determining that the user has not acknowledged the alarm within a predetermined time period, output two or more alerts in which each respective successive alert of the two or more alerts has at least one of a greater amplitude, frequency, or duration than each respective prior alert of the two or more alerts, wherein the two or more alerts are output until the user has acknowledged at least one of the two or more alerts.

14. The device of claim 13, wherein the sensor is configured to detect body movements.

15. The device of claim 13, wherein the sensor is an accelerometer.

16. The device of claim 15, wherein the accelerometer is configured to detect rhythmic bodily movements associated with heart rate.

17. The device of claim 15, wherein the accelerometer is configured to detect rhythmic bodily movements associated with respiration.

18. The device of claim 13, wherein the controller is configured to output the two or more alerts until the user has acknowledged at least one of the two or more alerts.

19. The device of claim 13, wherein the at least one physiological parameter of the user comprises user limb movement data.

20. The device of claim 13, wherein the at least one physiological parameter of the user comprises at least one of galvanic skin response data, pulse oxymetry data, heart rate data, or respiration data.

21. The device of claim 13, wherein the alarm comprises at least one of an audible alarm, a vibration alert, a blinking light-emitting diode, or a display of text.

22. The device of claim 13, wherein the two or more alerts comprise a plurality of audio or vibration alerts that are output until the user has acknowledged at least one of the plurality of audio or vibration alerts.

* * * * *